United States Patent [19]

Swann et al.

[11] Patent Number: 4,897,349

[45] Date of Patent: Jan. 30, 1990

[54] BIOSYNTHESIS OF HYALURONIC ACID

[75] Inventors: David A. Swann, Lexington; Bernard P. Sullivan, Andover, both of Mass.; Gordon Jamieson; Kenneth R. Richardson; Tarlach Singh, all of Cleveland, United Kingdom

[73] Assignee: MedChem Products, Inc., Woburn, Mass.

[21] Appl. No.: 344,896

[22] Filed: Apr. 28, 1989

[51] Int. Cl.$^4$ .................... C12P 19/04; C12R 1/46
[52] U.S. Cl. ...................... 435/101; 435/170; 435/802; 435/818; 435/885
[58] Field of Search ............. 435/101, 885, 170, 802, 435/818

[56] References Cited

U.S. PATENT DOCUMENTS

| 3,860,489 | 1/1975 | Cooper III | 435/802 |
| 4,517,295 | 5/1985 | Bracke et al. | 435/101 |
| 4,780,414 | 10/1988 | Nimrod et al. | 435/818 |
| 4,782,024 | 11/1988 | Scott et al. | 435/818 |
| 4,784,990 | 11/1988 | Nimrod et al. | 435/101 |
| 4,788,144 | 11/1988 | McMullen | 435/818 |
| 4,801,539 | 1/1989 | Akasaka et al. | 435/101 |

FOREIGN PATENT DOCUMENTS

| 0006690 | 6/1977 | Japan | 435/818 |
| 0032893 | 2/1987 | Japan | 435/101 |
| 0028398 | 2/1988 | Japan | 435/101 |
| 0595441 | 2/1978 | Switzerland | 435/818 |

Primary Examiner—Herbert J. Lilling
Attorney, Agent, or Firm—Kane, Dalsimer, Sullivan, Kurucz, Levy, Eisele and Richard

[57] ABSTRACT

Improved overall yields of hyaluronic acid are obtained by controlling the oxygen available for metabolism by a hyaluronic acid producing microorganism. Relatively high oxygen concentrations are made available during the initial exponential growth phase of the cultivated microorganism, until a predetermined growth has been reached. At this time, the available oxygen is limited to stimulate a disproportionately larger production of the desired hyaluronic acid.

4 Claims, 2 Drawing Sheets

BIOSYNTHESIS OF HYALURONIC ACID

BACKGROUND OF THE INVENTION

1. Field of the Invention

The invention relates to hyaluronic acid and more particularly to the microbiological transformation of organic precursors into hyaluronic acid.

2. Brief Description of the Prior Art

Hyaluronic acid is the main component of the capsules formed by many strains of group A and by most strains of group C Streotococci. These microorganisms can assimilate glucose and under a variety of environmental conditions produce hyaluronic acid as a secondary metabolite; see for example the description given by Roseman et al., J. Biol. Chem. 203, 213 (1953).

The synthesis of hyaluronic acid by Streptococci is influenced by many variable factors, genetic as well as nutritional. In spite of many reports concerning the optimal conditions for hyaluronic acid production by Streptoccocci, not all of the conditions have heretofore been defined.

In regard to genetic factors, it is well known that certain strains of Streptococci produce hyaluronic acid in one period of their life and secrete hyaluronidase at a later time; see for example: Pike, R. M., *Hyaluronidase and Hyaluronic Acid of group A Streptococci.*, Am. J. Med., 4, 468. (1948). As one would expect, when extracellular hyaluronidase negative strains of Streptococci are grown under controlled conditions, yields of a high molecular weight hyaluronic acid are reportedly obtained; see U.S. Pat. No. 4,782,046 of Brown, et al.

The environmental factors necessary for the production of hyaluronic acid by Streptococci have been reported as including both anaerobic fermentation conditions and aerobic fermentation conditions. Under anaerobic conditions, hyaluronic acid yields of from 0.3 to 1.0 gms/liter of fermentation media have been reported; see for example Thonard et al., J. Biol. Chem., 239, 726 (1964); Holmstrom et al., Microbio., 15, 1409 (1967); and Kjems and Lebech, Acta Path. Microbiol. Scand., 84, 162 (1976). The hyaluronic acid obtained under these procedures generally has a weight average molecular weight of 700,000 or less [calculated from the limiting viscosity number; method of Laurent et al, Biochimica et Biophysica Acta, 42, 476 (1960)]. Under aerobic fermentation conditions, a product with a higher weight average molecular weight (circa. 2,000,000 or more) is reportedly obtained in comparable overall yields; see Japanese Patent publication Kokai No. 58-056692 (Apr. 4, 1983) filed by Akasaka et al. The higher molecular weight product is advantageous for a number of commercial purposes.

At the time of the Akasaka et al. publication, a debate arose as to the role of aeration in the culturing of the hyaluronic acid producing Streptococci. An earlier publication of Cleary et al., J. of Bacteriology, 140, No.3, pgs 1090-1097 (1979) had suggested that hyaluronic acid functioned as an oxygen impervious shield, protecting the Streptococcus from the toxic effect of molecular oxygen. Thus, as a cell protective mechanism it was thought that aerobic conditions stimulated hyaluronic acid production. There are artisans who subscribe to this theory, and data can be pointed to in support of the proposition. In fact our own work may be at least in-part supportive of the theory.

However, Bracke et al. (U.S. Pat. No. 4,517,295; May 14, 1985) discovered that improved yields of hyaluronic acid (reported as "a minimum" of 2 gms/liter of culture broth) were obtained under carbon dioxide enriched, anaerobic conditions. There is therefore controversy as to the role of aerobic and anaerobic conditions in the biosynthesis of hyaluronic acid employing the Streptococcus organism.

We have discovered that even higher yields of hyaluronic acid can be produced by Streptococcus by and through control of aerobic conditions during cultivation of the microorganism. Although we are not to be bound by any theory of operation, we believe the process of the invention and its advantageous yields may be due in part to the following explanation.

Streptococci, which are known pathogens, are preferably, cultivated in closed systems. The system may be initially charged with nutrients and sealed. A seed culture is introduced into the sealed system and cultivation encouraged. Metabolic products (other than carbon dioxide) are usually not removed from the system during cultivation.

In the aerobic cultivation of Streptococci in a closed system, charged with a total requirement of nutrient at the start of cultivation, there is a typical sequence of growth and metabolic events. Initially, a so-called "lag phase" occurs during which there is a linear growth of the microorganism at a relatively slow rate. The culture medium during this lag phase generally has a high dissolved oxygen content because there is a prevailing tendency to saturate the liquid nutrient medium with dissolved oxygen prior to initiating fermentation. In the lag phase there is usually a relatively high production of hyaluronic acid by the microorganism, in proportion to the biomass, i.e.; the weight of viable cells present. This may be due at least in part, to the high oxygen presence (Cleary et al. supra.).

At some point, usually after about 4 to 8 hours into the lag phase, there occurs exponential cell growth with an observable increase in the total biomass (termed the exponential phase). During the lag and exponential phases the microorganism is utilizing nutrient and oxygen for cell growth (division), maintenance and secondary metabolism. During the exponential phase hyaluronic acid is produced and secreted into the culture medium in substantially parallel proportion to the increase in biomass. This is in contrast to the higher proportional production of hyaluronic acid associated with the lag phase and could be expected since the cell activity is focused on use of nutrients for cell division and not secondary metabolism. The cell metabolism is primarily directed toward reproduction, in the exponential phase.

As nutrient is depleted from the growth medium, growth can no longer be sustained exponentially. The increase in cellular biomass peaks, levels off in a so-called "stationary phase" and then declines in a terminal or death phase as the microorganisms die faster than they reproduce. Nutrient is depleted to the point where only cell maintenance continues, for cell viability.

From all of the above, the skilled artisan might surmise that the best overall yields of hyaluronic acid by the Strectococcus would result if one were to cultivate the oxygen-sensitive microorganism under anaerobic conditions during the exponential phase to obtain an optimal exponential phase increase in biomass and then to provide aeration to provoke the higher population of the microorganism to maximize hyaluronic acid secretion. It was our discovery that a different sequence provides the better overall yields of the desired product, and that strict anaerobic conditions are not required or desired at all. Indeed, if one initiates the cultivation and the start of the exponential phase of growth in the presence of relatively high oxygen concentrations and then subsequently starves the growing biomass of oxygen during the exponential growth phase, higher overall yields of hyaluronic acid are obtained. The reduction of oxygen availability at a point of time during exponential growth actually raises the level of hyaluronic acid production, by the microorganism.

SUMMARY OF THE INVENTION

The invention comprises a process for the biosynthesis of hyaluronic acid, which comprises;

providing a strain of hyaluronic acid producing, hyaluronidase—negative microorganism;

providing a liquid nutrient medium for culturing the provided microorganism;

inoculating the provided medium with the provided microorganism;

cultivating the inoculate microorganism under aerobic conditions to a point of exponential growth wherein the biomass of the microorganism has increased by a factor of from 2 to about 10 times, based on dry weight of cells; and cultivating the increased biomass of microorganism under aerobic conditions of reduced dissolved oxygen availability;

whereby the microorganisms produce a disproportionately larger amount of hyaluronic acid during the exponential growth phase, than they would have in the absence of the reduced oxygen availability condition.

The process of the invention produces a greater overall yield of hyaluronic acid from a given proportion of nutrient (organic presursors of the hyaluronic acid).

DETAILED DESCRIPTION OF THE PREFERRED EMBODIMENTS OF THE INVENTION

Apparatus

Figure 1:
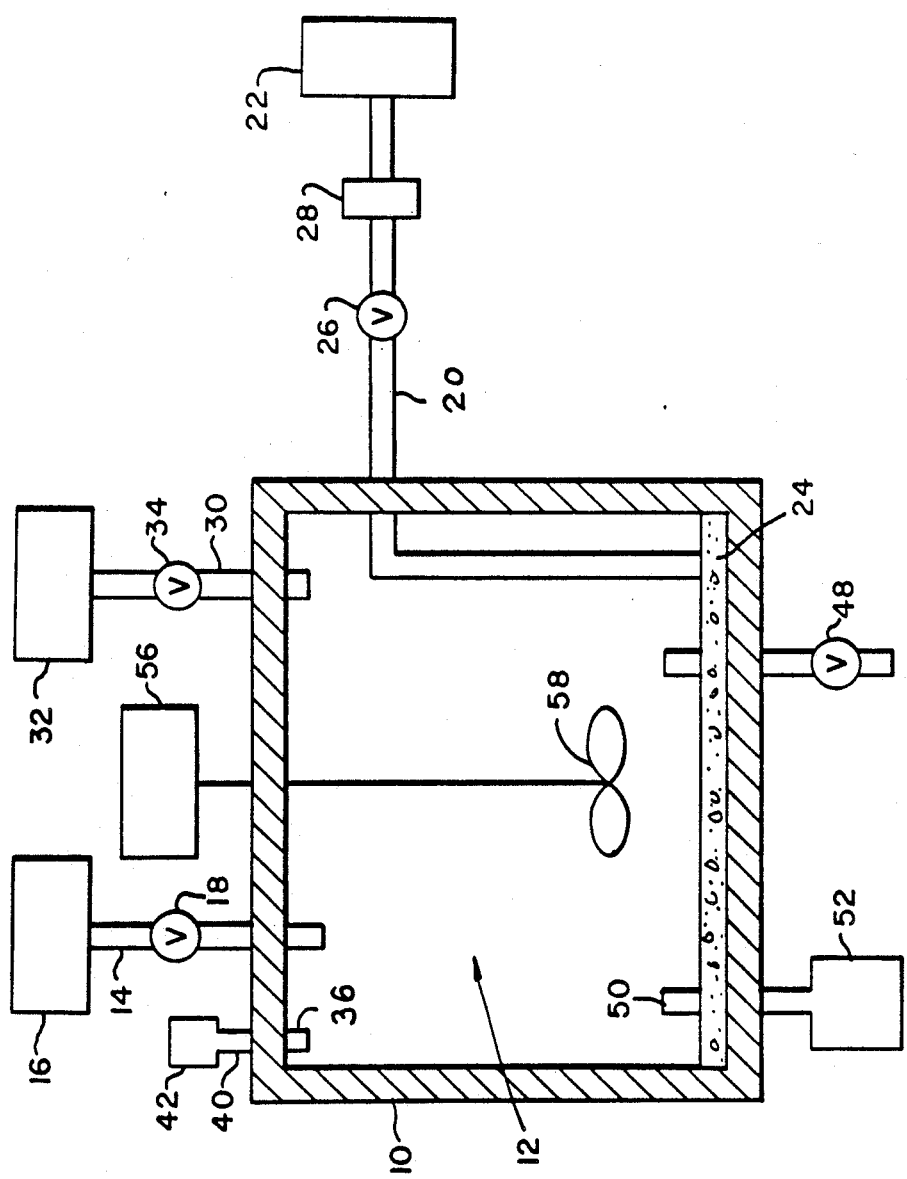
FIG. 1 is a schematic of apparatus employed to carry out an embodiment process of the invention.

Any of the conventional fermenter vessels commonly used in the cultivation of pathogenic microorganisms may be employed in the method of the present invention. The apparatus described herein is representative. Referring first to FIG. 1, there is seen a schematic drawing of apparatus for carrying out a preferred embodiment process of the invention. A fermentation vessel 10 of predetermined volume capacity is completely closed and sealed from the atmosphere or external environment. The vessel 10 shown in cross-section defines an interior, sealed fermentation chamber 12. Access to the chamber 12 is achieved through conduit 14 which is an inlet for sterile culture medium from reservoir 16. Valve means 18 controls the access. Conduit 20 is a gas inlet for aeration of culture medium charged to the chamber 12 and provides a means of carrying oxygen containing gases from gas reservoir 22 to the chamber 12, preferably through a glass frit 24 for diffusing micro bubbles into the culture medium. Valve means 26 on conduit 20 provides a means of controlling the rate and volume of gas entering chamber 12. A microbe filter 28 on conduit 20 prevents passage of cultivated microorganisms to the external environment and purifies the air or other oxygen containing gas carried into the chamber 12.

Conduit 30 provides access to the culture media in chamber 12 to provide pH adjusting reagents (alkali or acid) from a reservoir means 32 and is controlled by valve means 34. Conduit 36 provides a re-sealable access portal into the chamber 12 for sampling the chamber contents and is normally sealed to prevent the exit of contained materials. Conduit 40 is a gas vent, and includes a microbe filter 42. Valve means 48 provides a means for discharging the contents of the chamber 12 when so desired. Any number and kind of sensor lines may penetrate the vessel 10 for the determination of temperature, pH, dissolved oxygen content and like conditions of the internal environment of vessel 10. In the drawing of FIG. 1, only an oxygen sensor 50 and dissolved oxygen measuring apparatus 52 is shown for clarity of the drawing. A motor 56 provides a means to operate a means of agitation (mixer 58). The vessel 10 is preferably jacketed to provide heating and cooling means for operation of the fermenter to cultivate the microorganism.

Any conventional means of introducing dissolved oxygen into the nutrient media charged within chamber 12 may be used in carrying out the process of the invention; see for example the mechanical means described in the U.S. Pat. Nos. 4,204,042 and 4,643,972 both of which are incorporated herein by reference thereto. In general, conventional means include aeration and agitation of the nutrient media (commonly used in the aerobic - submerged cultural techniques and the so-called "air-lift" technique). Oxygen is preferably introduced into the nutrient media as a constituent of air, or in admixture with other gases, such as nitrogen.

A gas sparger for the introduction of an oxygen containing gas may take the form of a plenum with a plurality of gas orifices positioned about the periphery of chamber 12 at the base of the vessel 10. Although not critical, the orifices may have diameters ranging from about 0.05 mm to 100 mm, spaced apart from each other by distances of from about 0.50 to 10 mm.

For controlling the dissolved oxygen concentration in the nutrient media, any of the known and conventionally used techniques may be used. For example, methods such as changing the partial pressure of the oxygen by aerating with air, oxygen or mixtures thereof may be used. Changes in the gas contact area, contact time between gas and liquid phases (nutrient media), cultivation under elevated pressures or combinations of these factors may also be used. The geometry of the fermentation vessel 10 chamber 12 and the degree of mixing achieved within the vessel 10 may be used to control "stagnant" zones in the nutrient media. In this way dissolution of oxygen may be controlled by both vessel 10 design and degrees of agitation. A homogeneous mixing is advantageous.

The vessel 10 may be constructed in any desired size and configuration of any conventional material, such as glass or stainless steel 304 following accepted and good engineering practices. Generally, the vessel 10 will be substantially cylindrical with a chamber 12 having a height to diameter ratio within the range of from about 1:1 to about 4:1.

The Microorganism

There are a wide variety of group A and group C Streptococci known to be hyaluronic acid producing, hyaluronidase-negative; see for example the so-identified microorganisms in Faber, V., and Rosendal, K., 1954, *Streptococcal hyaluronidase: II. Studies on the production of hyaluronidase and hyaluronic acid by representatives of all types of hemolytic Streptococci belonging to group A.* Acta Path.Microbiol.Scand., Fasc. 2, 109–164. Preferred microorganisms which may be employed in the process of the invention are *S. zooepidemicus, S. equisimilis* or *S. pyogenes.* The most preferred species is *S. zooepidemicus* and the preferred strain is *S. zooepidemicus* (NCTC 7023) on deposit and freely available to the public from the National Culture Type Collection, 61 Colindale Ave., London NW9 5HT. It has been described as a hyaluronidase deficient hyaluronic acid producing strain by Mac Lennan, J. Gen. Microbiol 15: 485–491.

Nutrient Media

It has been said that from a nutritional viewpoint Streptococci are among the most complex species of bacteria in regard to their nutritional needs for culturing. However, the literature is replete with descriptions of nutrients and media required to cultivate these microorganisms and promote their production of hyaluronic acid. Such nutrient media comprise carbohydrates, vitamins, amino acids, inorganic salts and certain accessory substances. Representative of literature descriptions of the nutritional needs of the Streptococci are those found in Wilson, A. T., *Nucleic Acid Derivatives As Growth Factors For Certain Group A Hemolytic Streptococci,* Proc. Soc. Exp. Biol. and Med. 58, 249–254 (1945); and in Wilson, H., *Pantothenic Acid and the Growth of Streptococcus Hemolyticus.,* Brit. J. Exp. Path. 20, 330–341 (1939).

In general, sucrose and glucose serve equally well as carbohydrate sources for hyaluronic acid production. It has been reported that both the glycosamine and the glucuronic acid portion of hyaluronic acid are derived from glucose without breakdown of the glucose molecule. The glucose, although an essential building block for the hyaluronic acid polymer, is also an "energy source" for cell growth.

High extra-cellular glucose concentrations affect cell respiration. The respiration rate in the short term is reduced by higher concentrations of glucose. Generally, an initial glucose charge of from about 30 to about 85 g/l is used in the nutrient medium. The preferred process of the invention generally imposes a charge of glucose of approximately 60 g/l at the start of the fermentation. Advantageously, sufficient glucose is provided in the nutrient medium, calculated to produce from 1 to 3 gms/l of dry cell weight biomass and 3 to 6 gms/l of hyaluronic acid.

Nitrogen sources included in the nutrient media may be organic or inorganic nitrogen compounds, such as for example ammonium sulfate, ammonium chloride, ammonium phosphate, ammonium hydroxide, urea, glutamine, amino acids, peptone, hydrolysate of soy bean protein and the like.

In addition, there may also be added to the medium a suitable variety of inorganic salts advantageous for growth of the microorganisms, e.g. the sulfates, hydrochlorides, carbonates, nitrates, phosphates and acetates of for example calcium, potassium, sodium, magnesium, manganese, iron, copper and zinc. Also, amino acids, vitamins, and the like which are advantageous for growth of the microorganism. These nutrients may be used singly or in combination in amounts appreciated by skilled artisans.

A specific nutrient medium is described in the U.S. Pat. No. 4,517,295 (Bracke et al.). Other specific nutrient media which are advantageously used in the method of the invention include the following:

Medium A

A nutrient medium is prepared by mixing the following ingredients, in the indicated proportions per liter of water:

| | |
|---|---|
| 10–50 g | Yeast Extract |
| 1.3 g | $K_2SO_4$ |
| 1.0 g | $MgSO_4\ 7H_2O$ |
| 0.2 g | $Na_2\ SO_4$ |
| 5 mg | $CaCl_2\ 2\ H_2O$ |
| 5 mg | $Fe\ SO_4\ 7H_2O$ |
| 1 mg | $Mn\ SO_4\ 4H_2O$ |
| 1 mg | $Zn\ SO_4\ 7H_2O$ |
| 0.1 mg | $Cu\ SO_4\ 5H_2O$ |
| 1 ml of | $H_3PO_4$ (concentrated) |

The medium is sterilized by filtration through a 0.2 μm filter or by heating to a temperature of 121° C. for 20 minutes.

Generally, the pH of the medium is adjusted to within the range of 5 to about 8. The preferred pH range is 6.8 to 7.5. When the pH of the medium changes beyond the appropriate range during fermentation, it is possible to bring the pH of the medium back into such range by adding an appropriate amount of an acid or an alkali, as required to make the adjustment. An alkaline reagent may be an aqueous solution or suspension of alkali hydroxide, calcium carbonate, or the like, or ammonia gas, for example. Acid reagents such as dilute mineral acids, for example, hydrochloric acid may be used.

Process

Employing apparatus such as that represented in FIG. 1, the sterile nutrient medium is charged to the chamber 12 and heated to a temperature within the range of from about 30° to 40° C., preferably about 37° C. The microorganism is inoculated into the liquid nutrient medium and cultivated under aerobic conditions.

The aerobic conditions include an initial dissolved oxygen content in the nutrient medium of above 80 percent of saturation, up to 100 percent of saturation. This is generally achieved by introduction of air in the nutrient medium at a rate of 0.1–1.0 vvm (volumes per volume of nutrient medium) typically 0.4 vvm (i.e.; 1400 ml/min of air, into 3500 ml of culture). The desired level of dissolved oxygen content can usually be maintained by homogeneous mixing of the culture medium, for example by agitation at 250–1500 rpm, typically 900 rpm, (impeller configuration; lower vaned-disc and upper, a turbine or 2 turbines).

A factor affecting the aeration and agitation of the fermentation mixture is the culture viscosity. Since the culture viscosity increases logarithmically rather than linearly with concentration, the degree of aeration/agitation may therefore have to be adjusted during the course of fermentation to take this factor into account. Alternately, one can start the fermentation with a low viscosity mixture, so that as fermentation proceeds, little or no adjustment may be needed.

S. zooepidemicus (NCTC 7023) in a low or high oxygen environment is homo-fermentative, the metabolic end products being L-lactic and acetic acids respectively, according to the scheme:

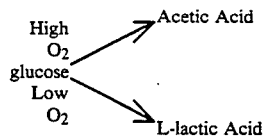

At intermediate oxygen concentrations, e.g. 10-100 mm Hg, S. zooepidemicus (NCTC 7023) is hetero-fermentative and both lactic and acetic acids are produced, with lactic acid the dominant species.

A further consequence of "acetic acid" metabolism, is an increased cell yield, i.e., one tends to produce cells rather than product. When conditions result in "lactic acid" producing metabolism, one tends to produce hyaluronic acid product rather than reproduced cells. Thus, metabolism is according to the scheme:

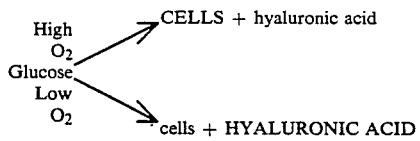

wherein the upper case printing indicates the dominant product (cells or hyaluronic acid). This is a simplification of the equilibrium forming the basis of the present invention, but does illustrate the need to control oxygen availability in order to control cell production and hence promote hyaluronic acid production. Under both high and low oxygen conditions, exponential growth of the microorganism will occur and can be observed by a periodic sampling of the biomass dry weight. A specific growth rate of cells (R) may be calculated according to the following formula by determining the cell concentration at periodic cultivation times.

$$R = \frac{2.302 \cdot \log 10 \ (X_t/X_o)}{t}$$

where
$X_o$ = initial cell concentration;
$X_t$ = cell concentration time after t hours; and
t = cultivation time, (hr).

When it is calculated that the growth rate is exponential, i.e.; the biomass is increasing exponentially, the operator may then select a point in time when the biomass has increased by at least 2-fold (more than immediately following inoculation) but less than about 10-fold. At a selected point within this period, the dissolved oxygen content of the nutrient medium is reduced or allowed to decline below 80 percent of saturation, advantageously within a range of from about 0 percent to about 5 percent of saturation. This provides a condition wherein the exponentially growing microorganism may be observed to produce a disproportionately higher level of hyaluronic acid, than one would expect from the weight of the producing biomass.

As mentioned above, there are many techniques known in the art for controlling the dissolved oxygen content in nutrient media, and any of the known methods may be employed to reduce the oxygen content of the liquid medium to the required level found in the method of the present invention. For example, a reduction in the gas contact area or the contact time between gas/liquid phases may be employed, i.e.; reductions in the gas volume and/or degree of agitation of the fermenting mixture. In a preferred embodiment process of the invention, the growth rate of the increasing biomass is used so that the microorganism consumes more oxygen than is being introduced into the liquid nutrient medium. This will automatically reduce the dissolved oxygen content of the medium to the desired levels. By constantly monitoring the growth rate and the decreasing oxygen content, one can arrive at the point in the fermentation when the higher hyaluronic acid production rate is triggered, while exponential growth rates are substantially sustained.

Regarding the duration of cultivation, the microorganism is cultivated at least until the yield of hyaluronic acid is maximal. Generally, the desired objective can be accomplished by cultivating the microorganism for from less than 24 to 144 hours. At the cessation of the process, determined via alkali consumption, dissolved oxygen tension level, or $CO_2$ production, the culture may be killed and removed for extraction. Hyaluronic acid as elaborated in the fermentation broth according to this invention can be recovered from the broth, either independently or as a mixture, by the known purification procedures such as chromatography using an ion exchange resin or activated carbon; precipitation, solvent extraction, and like methods.

Specific techniques for the termination and separation of the microorganisms from the desired hyaluronic acid are well known; see for example the techniques described in the Japanese Patent Sho No. 63-12293 and U.S. Pat. Nos. 4,517,295 and 4,780,414 incorporated herein by reference thereto.

Methods of physically separating the hyaluronic acid from the killed or dying microorganism are also well known in the art; see for example the methods described by Nimrod et al. in U.S. Pat. No. 4,780,414, incorporated herein by reference thereto.

The following examples and preparations describe the manner and process of making and using the invention and set forth the best mode contemplated by the inventors of carrying out the invention but are not to be construed as limiting the invention. Where reported, the following tests were carried out:

Molecular Weight ($M_w$)

Molecular weights reported are weight average molecular weights, determined by calculation from the limiting viscosity number using the equation of Laurent et al., Biochimica et Biophysics Acts., 42: 476-485 (1960).

Kinematic Viscosity (KV)

Determined at a temperature of 25° C. and a shear rate of 1 sec$^{-1}$ using a Brookfield Digital Viscometer Model RVTDCP with cone spindle CP52.

Intrinsic Viscosity (IV)

The intrinsic viscosity was measured using a Cannon Ubbelohde semi-micro dilution viscometer, size 75, at 37° C. and is reported in milliliters/gram (ml/g).

Dissolved Oxygen (D.O.)

The concentration of dissolved oxygen may be determined with a Beckman D.O. meter and is reported as a percentage of air saturation (dissolved oxygen tension).

PREPARATION 1

Inoculum

An inoculum was made by adding 200 ml of a medium to a flask. The medium consists of the following per liter of water:
- 10 gm yeast autolysate
- 2.0 gm $KH_2PO_4$
- 0.2 gm $MgSO_4 7H_2O$
- 0.05 gm $MnSO_4.4H_2O$
- 5 mg $FeSO_4 7H_2O$
- 1 ml trace elements The composition of the trace elements solution (as the sulfate salts) per liter was:
- 720 mg calcium
- 24 mg manganese
- 22 mg zinc
- 5 mg copper Adjust pH to 7.2 (with either 2N NaOH or 2N HCl) and autoclave at 121° C. for 15 min. Once the flask is cool the following are added aseptically per liter:
40 ml of sterile buffer (at pH 7.2) containing
- 12.5 gm $NaHCO_3$
- 15.98 gm $NaH_2PO_4.H_2O$
- 36.76 gm $Na_2HPO_4$ and 12 ml of 50% (w/v) sterile glucose.

Stock cultures of *S. zooepidemicus* (NCTC 7023) stored as glycerol stocks or lyophylised cultures are streaked out on Todd Hewitt broth agar slopes, grown at 37° C. and stored at 4° C. until use. To add the culture to the inoculum flask, cells on a Todd Hewitt broth slope are aseptically resuspended in 5 ml Ringer's solution which consists of per
- 2.25 gm NaCl
- 0.105 gm KCl
- 0.12 gm $CaCl_2.2H_2O$
- 0.05 gm $NaHCO_3$ with the pH adjusted to 7.0 (with 2N HCl or 2N NaOH).

The cell suspension (2.5 ml) is then aseptically added to the inoculum flask. The flask is then incubated at 37° C. for hours before being checked for culture purity and used to inoculate the fermenter.

EXAMPLE 1

A 200 ml proportion of the inoculum of Preparation 1, supra. was aseptically added to 3 liters of a nutrient solution composition consisting of
- 33 gm glucose
- 1.3 gm $K_2SO_4$
- 1.0 gm $MgSO_4.7H_2O$
- 1.0 ml concentrated $H_3PO_4$ (sp. grav. 1.65)
- 5.0 mg $FeS_4.7H_2O$ and
- 2.5 ml trace elements solution per liter of solution.

The trace elements solution was as described in Preparation 1, supra

The microorganism was cultivated for a period of 18 hours. The cultivation was carried out under well aerated conditions (0.4 vvm of air) and was well stirred at 900 rpm. Even with this regime the growth is such as to reduce the dissolved oxygen tension to zero for a number of hours, e.g.; between 2 and 6 hours during the exponential growth phase. At the end of the 18 hour period of residence time in the fermenter, 3.0 gm/l of microorganism cells (dry weight) are produced along with 1.1 gm/l of hyaluronic acid. Physical tests carried out on the product acid are set forth in Table 2, below.

EXAMPLE 2

Figure 2:
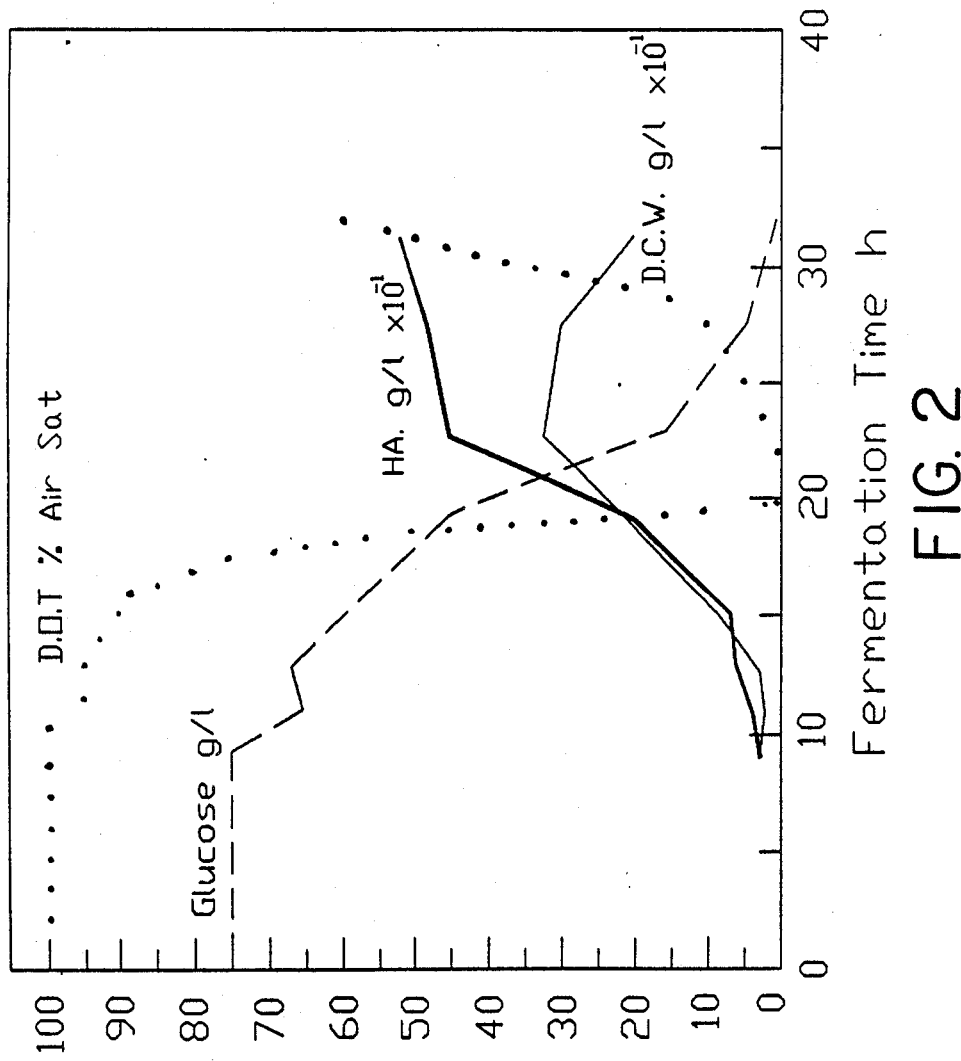
FIG. 2 is a graphical representation of analytical results obtained upon chemical and physical analysis of the culture medium of Example 2, during the carrying out of an embodiment process of the invention.

The procedure of Example 1, supra, was repeated with the exception that the initial glucose concentration was increased to 75 gm/l. After a 32 hours residence time 2 gm/l of cells (dry weight) were produced along with 5.1 gm/l of hyaluronic acid. The dry cell weight, dissolved oxygen content, nutrient (glucose) level and hyaluronic acid contents of the fermenting mixture as determined periodically during fermentation are set forth in the Table 1 below and are shown in the drawing of FIG. 2. The microorganism was killed and the hyaluronic acid separated. The purified hyaluronic acid (HA) was characterized by analytical tests, reported in Table 2, below.

TABLE 1

| Hours | Dissolved Oxygen (% of saturation) | Glucose (gm/L) | Cells (gm/L Dry Wgt) | Hyaluronic Acid (gm/L) |
|---|---|---|---|---|
| 0.0 | 100 | 75 | — | — |
| 7.5 | 100 | — | — | — |
| 8.0 | 100 | 75 | 0.30 | 0.30 |
| 10.0 | 100 | — | — | — |
| 11.0 | 95 | 65 | 0.20 | 0.44 |
| 13.0 | 95 | 66 | 0.30 | 0.60 |
| 15.0 | 90 | — | 0.90 | 0.68 |
| 16.0 | 85 | — | — | — |
| 17.0 | 75 | — | — | — |
| 18.0 | 50 | — | — | — |
| 19.0 | 10 | 45 | 2.10 | 2.00 |
| 19.5 | 0 | — | — | — |
| 23.0 | 0 | 16 | 3.32 | 4.50 |
| 25.0 | 5 | — | — | — |
| 27.0 | 10 | 4.5 | 3.00 | 4.80 |
| 28.0 | 15 | — | — | — |
| 32.0 | 60 | 0.2 | 2.00 | 5.10 |

EXAMPLE 3

The procedure followed was as described in Example 2 supra. except in this case the pH was controlled with a 17% ammonia solution and the medium supplemented with 0.1 gm/l of $Na_2SO_4$. The starting glucose concentration was 55 gm/l. After 31.25 hours residence time, 2.5 gm/l of cells (dry weight) were produced and 1.2 gm/l of hyaluronic acid.

EXAMPLE 4

The procedure followed was as described in Example 2 supra. except a residence time of 23 hours in the fermenter produced 1.0 gm/l of cells (dry weight) and 3.7 gm/l of hyaluronic acid.

EXAMPLE 5

The procedure followed was as described in Example 2 supra. except a residence time of 22.5 hours in the fermenter produced 2.3 gm/l of cells (dry weight) and 3.3 gm/l of hyaluronic acid. The physical test results characterizing the product acid are set forth on Table 2, below.

EXAMPLE 6

The procedure followed was as described in Example 2 supra., except that the initial glucose concentration was 58 gm/l. A residence time of 17 hours produced 2.0 gm/l of cells (dry weight) and 3.3 gm/l of hyaluronic acid. The physical test results characterizing the product acid are set forth in Table 2, below.

EXAMPLE 7

The procedure followed was as described in Example 2 supra. except a residence time of 21 hours produced 1.3 gm/l of cells (dry weight) and 5.6 gm/l of hyaluronic acid. The physical test results characterizing the product acid are set forth in Table 2, below.

TABLE 2

| Example No | HA Wet Weight (gm) | HA (%) | IV | HA conc. (mg/ml) | KV (cSt) | Protein (ppm) |
|---|---|---|---|---|---|---|
| 1 | 2.2 | 9 | 3226 | 9.57 | 29,912 | 57 |
| 5 | 2.0 | 23 | 3025 | 10.07 | 30,609 | 5 |
| 6 | 2.0 | 33 | 2803 | 11.43 | 40,099 | 18 |
| 7 | 2.05 | 34 | 3799 | 11.33 | 67,739 | 1 |

From the above Examples, we have determined that higher yields of hyaluronic acid are obtained from a given mass of hyaluronic acid producing microorganism by a controlled growth, which growth serves also to control the dissolved oxygen content of the liquid nutrient medium. By a reduction of the available oxygen at a critical stage of the exponentially growing biomass, the microorganism is made to respond with higher production rates of hyaluronic acid then it would normally produce at higher dissolved oxygen levels. Although we are not to be bound by a theoretical reason for the observed response, it may be that the process of the invention through oxygen deprivation promotes lactic acid and hyaluronic acid production at this time. Higher levels of dissolved oxygen stimulate the microorganism to produce acetic acid and less hyaluronic acid while energy is expended on cell division.

What is claimed is:

1. A process for the biosynthesis of hyaluronic acid, which comprises;
   providing a strain of hyaluronic acid producing, hyaluronidase - negative microorganism;
   providing a liquid nutrient medium for culturing the provided microorganism;
   inoculating the provided medium with the provided microorganism;
   cultivating the inoculate microorganism under aerobic conditions to a point of exponential growth wherein the biomass of the microorganism has increased by a factor of from 2 to about 10 times, based on dry weight of cells; and
   cultivating the increased biomass of microorganism under aerobic conditions of reduced dissolved oxygen availability;
   whereby the microorganism produces a disproportionately larger amount of hyaluronic acid during the exponential growth phase, than it would have in the absence of the reduced oxygen availability condition.

2. The process of claim 1 wherein the microorganism is *S. zooepidemicus* (NCTC 7023).

3. The process of claim 1 wherein the nutrient includes as a source of nitrogen, yeast autolysate.

4. The process of claim 1 wherein the aerobic conditions include a dissolved oxygen content of more than about 80 percent of saturation and the reduced oxygen availability is a dissolved oxygen content of less than percent of saturation.

* * * * *